(12) United States Patent
Mlynczak et al.

(10) Patent No.: US 11,089,995 B2
(45) Date of Patent: Aug. 17, 2021

(54) METHOD AND SYSTEM FOR IDENTIFYING RESPIRATORY EVENTS

(71) Applicant: CLEBRE Spólka z o.o., Olsztyn (PL)

(72) Inventors: Marcel Mlynczak, Olsztyn (PL); Maciej Migacz, Olsztyn (PL); Wojciech Kukwa, Olsztyn (PL)

(73) Assignee: CLEBRE SPÓLKA Z O.O., Olsztyn (PL)

( * ) Notice: Subject to any disclaimer, the term of this patent is extended or adjusted under 35 U.S.C. 154(b) by 121 days.

(21) Appl. No.: 16/092,585

(22) PCT Filed: Mar. 23, 2017

(86) PCT No.: PCT/EP2017/056906
§ 371 (c)(1),
(2) Date: Oct. 10, 2018

(87) PCT Pub. No.: WO2017/178205
PCT Pub. Date: Oct. 19, 2017

(65) Prior Publication Data
US 2019/0167186 A1    Jun. 6, 2019

(30) Foreign Application Priority Data

Apr. 15, 2016    (EP) .................................... 16165682

(51) Int. Cl.
*A61B 5/00*    (2006.01)
*A61B 5/113*    (2006.01)
(Continued)

(52) U.S. Cl.
CPC .......... *A61B 5/4818* (2013.01); *A61B 5/0004* (2013.01); *A61B 5/0823* (2013.01);
(Continued)

(58) Field of Classification Search
CPC ................ A61B 5/0004; A61B 5/0832; A61B 5/0826; A61B 5/113; A61B 5/4806;
(Continued)

(56) References Cited

U.S. PATENT DOCUMENTS

| | | | |
|---|---|---|---|
| 5,953,713 A | 9/1999 | Behbehani et al. | |
| 7,510,531 B2 * | 3/2009 | Lee | A61B 5/0031 600/534 |
| 8,775,340 B2 * | 7/2014 | Waxman | A61B 5/08 706/20 |

(Continued)

FOREIGN PATENT DOCUMENTS

WO    2015057709 A1    4/2015

OTHER PUBLICATIONS

International Search Report dated Oct. 19, 2017 in parent International application PCT/EP201710569006.
Written Opinion of the International Searching Authority dated Oct. 19, 2017 in parent International application PCT/EP2017/0569006.
(Continued)

*Primary Examiner* — Carl H Layno
*Assistant Examiner* — Jane C Kalinock
(74) *Attorney, Agent, or Firm* — Polson Intellectual Property Law, PC; Margaret Polson; Christopher Sylvain

(57) ABSTRACT

The present disclosure relates to a method and a system for examining respiratory disorders whereby signals coming from the examined person are recorded by a wireless sensor equipped with a microphone and an accelerometer and then sent to a monitoring station. The monitoring station receives a digital data stream from the wireless sensor, cuts out respiratory episodes from the signal and, using a classification assembly constructed from three independent detection modules, classifies a respiratory episode as being normal or as snoring as well as determines the occurrence of apnoea.

16 Claims, 5 Drawing Sheets

(51) Int. Cl.
    *A61B 7/00*          (2006.01)
    *A61B 5/1455*      (2006.01)
    *A61B 5/08*         (2006.01)

(52) U.S. Cl.
    CPC ............ *A61B 5/0826* (2013.01); *A61B 5/113* (2013.01); *A61B 5/14551* (2013.01); *A61B 5/7264* (2013.01); *A61B 5/7282* (2013.01); *A61B 5/7455* (2013.01); *A61B 7/003* (2013.01); *A61B 2562/0204* (2013.01)

(58) Field of Classification Search
    CPC ................ A61B 5/4809; A61B 5/4812; A61B 5/4815; A61B 5/4818; A61B 5/4821; A61B 5/7264; A61B 5/7282; A61B 5/7455; A61B 5/14551; A61B 7/003; A61B 2562/0204; G16H 50/20
    USPC ........................................................ 600/301
    See application file for complete search history.

(56) References Cited

U.S. PATENT DOCUMENTS

| | | | |
|---|---|---|---|
| 2010/0240982 A1* | 9/2010 | Westbrook | A61B 5/6831 600/391 |
| 2012/0029319 A1 | 2/2012 | La Guardia et al. | |
| 2013/0030257 A1* | 1/2013 | Nakata | G01S 7/003 600/301 |
| 2014/0188006 A1* | 7/2014 | Alshaer | A61B 7/003 600/586 |
| 2014/0213913 A1 | 7/2014 | Parfenova et al. | |
| 2016/0045161 A1* | 2/2016 | Alshaer | A61B 5/7282 600/538 |

\* cited by examiner

METHOD AND SYSTEM FOR IDENTIFYING RESPIRATORY EVENTS

BACKGROUND

The present disclosure relates to a method and a system for identifying respiratory events.

Respiratory disorders, including sleep disorders, have a negative impact on physical and mental health. Monitoring of events occurring during respiration is especially important during sleep when conscious intervention in the process of respiration is impossible. Sleep disorders in connection with respiratory disorders may lead to dangerous complications, which is why it is important to detect them early on. Some sleep disorders are shallow sleep and obstructive sleep apnoea. It is estimated that obstructive sleep apnoea affects at least 4% of men and 2% of women in the general population.

Nowadays, obstructive sleep apnoea and all other breathing-related sleep disorders are diagnosed by polysomnography, which is a gold standard. It allows determining the occurrence and length of the individual stages of sleep but requires a complex and cumbersome apparatus as well as the supervision of a competent person. However, something as simple as monitoring of the respiratory process of the examined person during their sleep allows diagnosing respiratory disorders during sleep such as obstructive sleep apnoea syndrome.

Polysomnography involves recording the EEG/EOG/EMG/ECG signals, airflow and oxygen saturation of the examined person during sleep. An example of such a device was disclosed in US2012029319 document which described a polysomnography examination method based on the remote management of apparatus. Unfortunately, such an examination is costly and requires a well-equipped laboratory and well-trained staff.

The published patent application US2014/0213913 disclosed a small device placed on the face of the examined person (near their nose) to measure their airflow, oxygen saturation and respiratory events. The measured values are transmitted wirelessly to a computer, registering and analyzing the results of measurements.

A system detecting apnoea was also disclosed in the patent application publication US2012/0071741. Apnoea is detected based on signals coming from a pulse oximeter and a microphone. The occurrence of snoring is provisionally determined on the basis of a signal from the microphone. Parameters calculated using the measurements are subjected to processing which includes the threshold function, weights assignment and summation. On that basis the occurrence of apnoea is determined.

Other embodiments include solutions using neural networks for the analysis of selected physiological parameters during sleep, e.g. the U.S. Pat. No. 5,953,713 patent disclosed a simultaneous analysis of the airflow and sound with the use of a transformation to the frequency domain of a signal representing the airflow during respiration as well as an analysis of this signal by means of a neural network.

There are systems which make it possible to diagnose obstructive sleep apnoea at home, but they also require the patient to appropriately install the sensors, transmitters, etc. This can make such devices difficult to use, despite their many advantages. An example of a system for diagnosing sleep apnoea which is available to patients is Watch-PAT manufactured by Itamar Medical Ltd.

SUMMARY

Proceeding from the forgoing, an aspect of the present disclosure is a method for identifying respiratory events whereby sound and motion signals, which are generated during respiration, are recorded by means of a wireless sensor equipped with a microphone sensor and a motion sensor. By using a microcontroller, the signals from sensors are converted into a digital data stream and the digital data stream is then sent to a monitoring station through a data transmission module. The present disclosure is characterized in that the data stream from the wireless sensor is received in the monitoring station and then the data representing the sound and motion signals are pre-filtered. In the segmentation module, the data representing the sound signal is divided into time windows and transformed to a frequency domain. Next, the signal is divided into segments corresponding to respiratory episodes on the basis of signal changes in the frequency domain in the time windows of the sound signal for specific sound signal frequencies. Subsequently, input vectors are created containing sound signal parameters in the time domain and in the frequency domain, statistical parameters specified on the basis of historical data as well as motion signals parameters in the time domain. Next, the input vector containing sound signal parameters is fed into the inputs of an assembly of at least three independent and different detection modules which have been designed to generate a signal classifying a respiratory event on the basis of a sound signal. Also, the vector containing motion signals parameters is fed into the input of a motion signal classification module which has been designed to generate a motion/position classification signal. In the next step, the data obtained at the output of the respiratory event classification module and the motion classification module are fed into an inference module at the output of which the respiratory event identification signal is output. The motion sensor may include an accelerometer/gyroscope or a combination of these two sensors. The motion signal includes all possible signals coming from the motion sensor.

Moreover, the method according to the present disclosure is characterized in that a respiratory event identification signal is generated in an independent detection module which is a multi-layer neural network whose weights have been set in such a manner that a signal, which differentiates respiratory disorders from normal respiration, is generated at the output of the neural network. The said signal contains a relative confidence factor of identification of respiratory disorders whereby in each detection module, the weights of neural networks have been selected independently from the weights of neural networks in other detection modules.

Furthermore, the method according to the present disclosure is characterized in that respiratory disorders signal is generated correspondingly to the reading of the detection module which generates an output signal with the highest confidence factor.

Furthermore, the method according to the present disclosure is characterized in that an input vector is created in which the statistical data refer to the population.

Furthermore, the method according to the present disclosure is characterized in that an input vector is created in which the statistical data refer to the historical data of the individual examined.

Furthermore, the method according to the present disclosure is characterized in that the wireless sensor is equipped with a vibratory signalling device.

Furthermore, the method according to the present disclosure is characterized in that the wireless sensor is equipped with a reflectance-based pulse oximeter.

Furthermore, an aspect of the present disclosure is a system for identifying respiratory events during examination, constructed from a wireless sensor comprising a microphone and a motion sensor, which record sound signals and motion signals generated during respiration, as well as with a microcontroller, which converts signals from the sensors into a digital data stream, and a wireless transmission module. Furthermore, the system comprises a monitoring station equipped with a wireless transmission module. Furthermore, the system comprises a signals pre-processing module which has been designed to pre-filter the data stream from the wireless transmission module, divided into time windows and transformed to a frequency domain for subsequent time windows, both for the sound signal and the motion signal. The system according to the present disclosure is characterized in that the monitoring station further comprises a segmentation module which has been designed to divide the sound signal and the motion signal into segments corresponding to respiratory episodes on the basis of sound signal changes in the frequency domain as well as into sound signal and motion signal time windows. Furthermore, the system according to the present disclosure comprises a transformation module which has been designed to create an input vector containing sound signal parameters in the time and frequency domains, historical data and statistical parameters, and a classification module consisting of at least three independent and different detection modules; which have been designed to generate a signal classifying a respiratory event on the basis of the input vector. Furthermore, the system contains a motion signal classification module, which has been designed to generate a position classification signal, and an inference module which has been designed in such a manner that a position identification output signal is output at its output.

Furthermore, the system according to the present disclosure is characterized in that the independent detection module is a multi-layer neural network whose weights have been set in such a manner that a signal, which differentiates respiratory disorders from normal respiration, is generated at the output of the neural network. The said signal contains a relative confidence factor of identification of respiratory disorders whereby in each detection module, the weights of neural networks have been selected independently from the weights of neural networks in other detection modules.

Furthermore, the system according to the present disclosure is characterized in that each detection module has a different set of weights of neural networks.

Furthermore, the system according to the present disclosure is characterized in that the inference module is adapted to generate a respiratory disorders signal based on the detection module with the highest confidence factor of the output.

Furthermore, the system according to the present disclosure is characterized in that the motion sensor is an accelerometer/gyroscope or a combination of these two sensors.

Furthermore, the system according to the present disclosure is characterized in that the sound signal is obtained from a microphone sensor or a signal coming from the motion sensor.

Furthermore, the system according to the present disclosure is characterized in that the wireless sensor is equipped with a vibratory signalling device.

Furthermore, the system according to the present disclosure is characterized in that the wireless sensor is equipped with a reflectance-based pulse oximeter.

BRIEF DESCRIPTION OF THE DRAWINGS

An embodiment of the present disclosure has been shown in greater detail in the following figures whereby.

DETAILED DESCRIPTION

Figure 1:
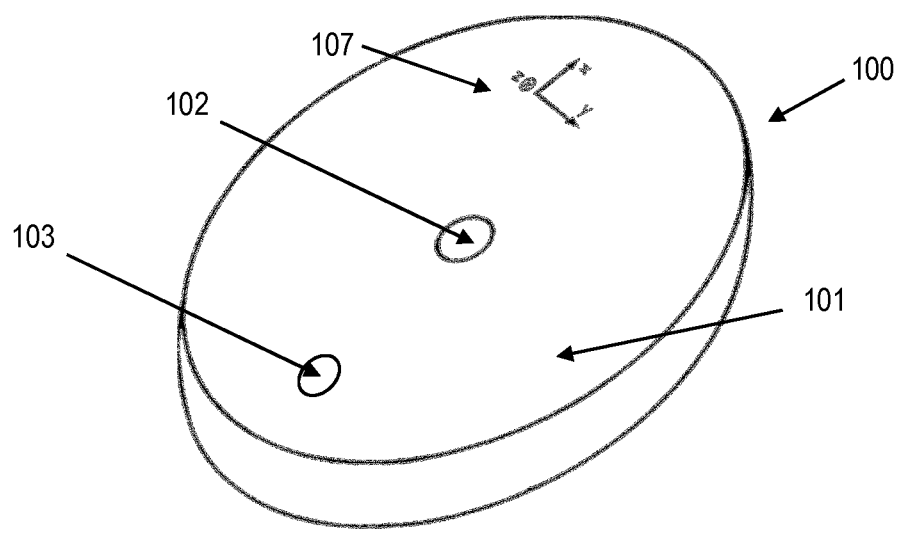
FIG. 1 shows a perspective view of the sensor of the system according to the present disclosure.

FIG. 1 shows a view of the wireless sensor (100) which constitutes part of the system according to the present disclosure where the housing (101) and the first opening (102) are visible. In the area of the opening (102) inside the housing, there is a microphone sensor. The opening (102) has a diameter of approx. 1 mm. There is also an assembly of motion sensors (for measuring acceleration and angular velocity) and a pulse oximeter (103) inside the housing. FIG. 1 additionally shows a schematic representation of the axes (107) along which the acceleration is measured.

Figure 2:
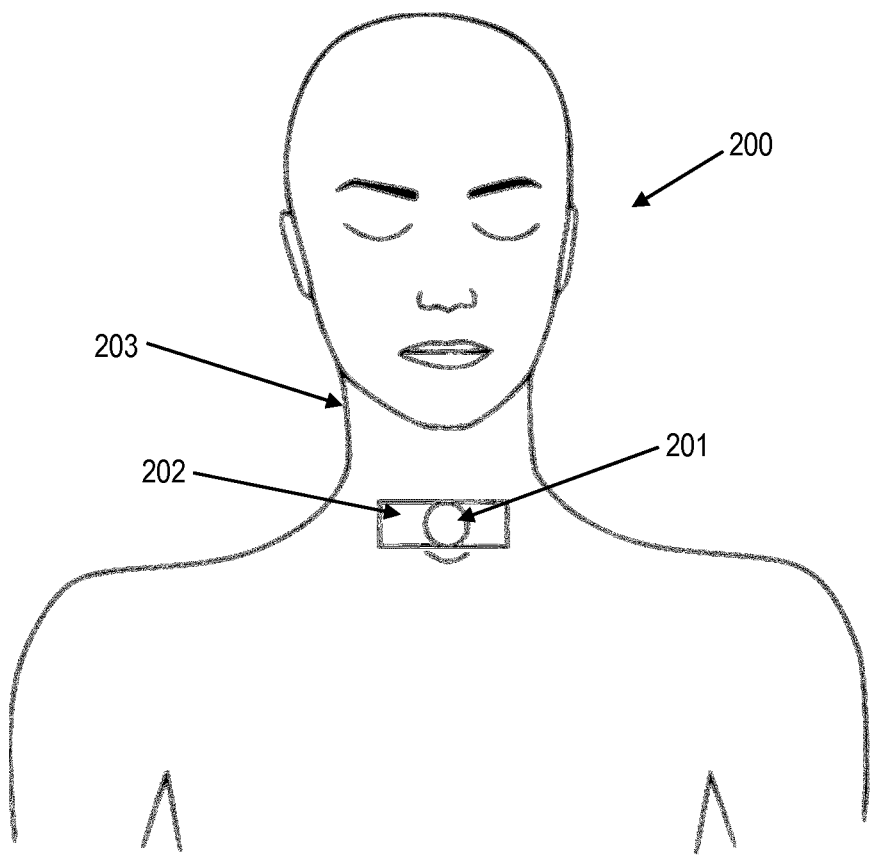
FIG. 2 shows the sensor of the system according to the present disclosure during an examination.

FIG. 2 shows the way the sensor (201) is placed for the purpose of examination. The sensor (201) is connected with the body of the examined person (200) in the front part of the neck (203), e.g. by means of a medical plaster (202) or in another appropriate way. Such a position of the sensor makes it possible to record good quality signals from the microphones and relate the signal from the motion sensor to the position of the body.

Figure 3:
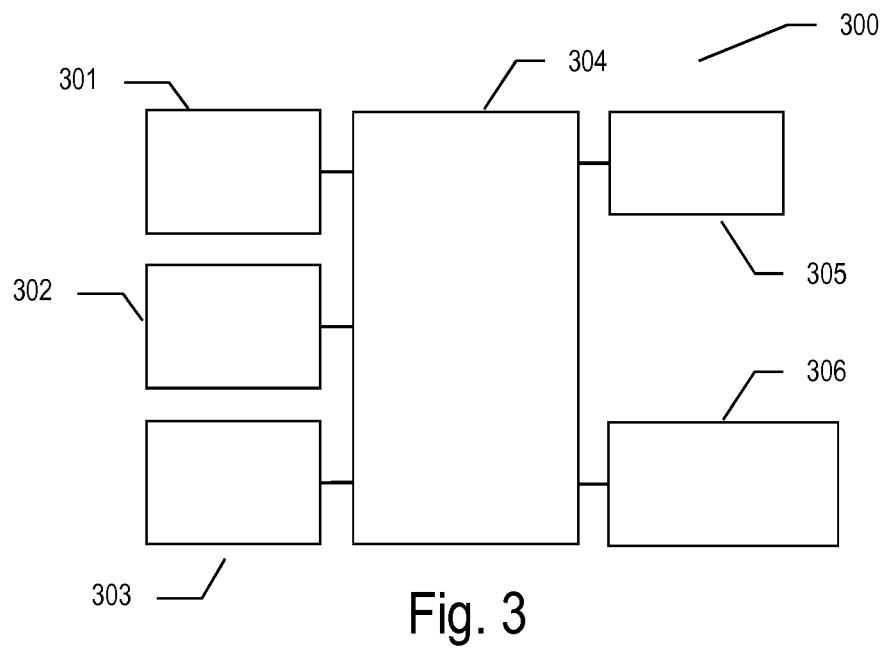
FIG. 3 shows a block diagram of the sensor of the system according to the present disclosure.

FIG. 3 shows a block diagram of the sensor of the system according to the present disclosure (300). The sensor has two types of transducers. The first type of transducer is a microphone (301) (the monitoring station may be equipped with a second microphone (302)). They are used to record the sound signals coming from the respiratory system of the examined person and the surroundings respectively. The second type of transducer is a three-axis motion sensor (303) which combines a three-axis acceleration sensor and a three-axis gyroscope for measuring six degrees of freedom. It makes it possible to determine the motions (activity) and the position of the sensor in space. This is used to determine the position of the body during respiratory episodes, including apnoea. The sensor also has a wireless communication system (305) which ensures communication with the latest mobile devices and low power consumption. Low power consumption is especially important for the mobile device which runs continuously throughout the whole measurement period. The operation of the sensor is controlled by a microcontroller-based controller (304), and the whole system is powered by a battery (306).

Figure 4:
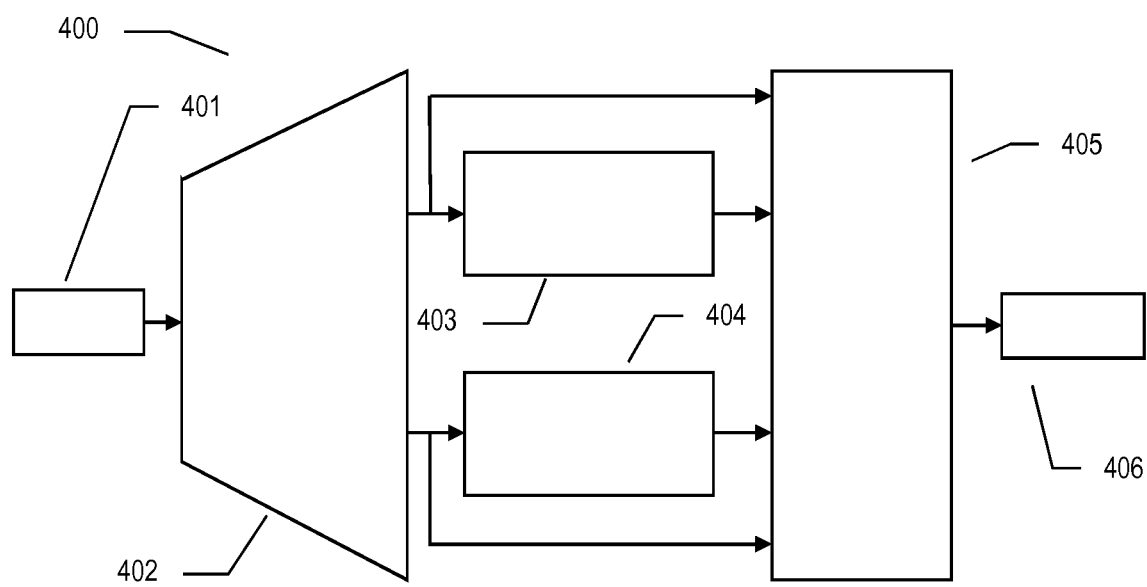
FIG. 4 shows a block diagram of the monitoring station of the system according to the present disclosure.

FIG. 4 shows a block diagram of the monitoring station of the system according to the present disclosure (400). The monitoring station includes a receiver module of the wireless communication system (401), a demultiplexer module (402) which separates sound signals from motion signals, a sound signal analysis circuit (403), and an analysis circuit of signals from the motion sensors (404). In addition, the monitoring station of the system according to the present disclosure includes an inference module (405) which analyzes the input signals and the output signals from the sound signal analysis circuit and the analysis circuit of signals from the motion sensors. The results of the analysis (406) are fed into the output of the inference module.

Figure 5:
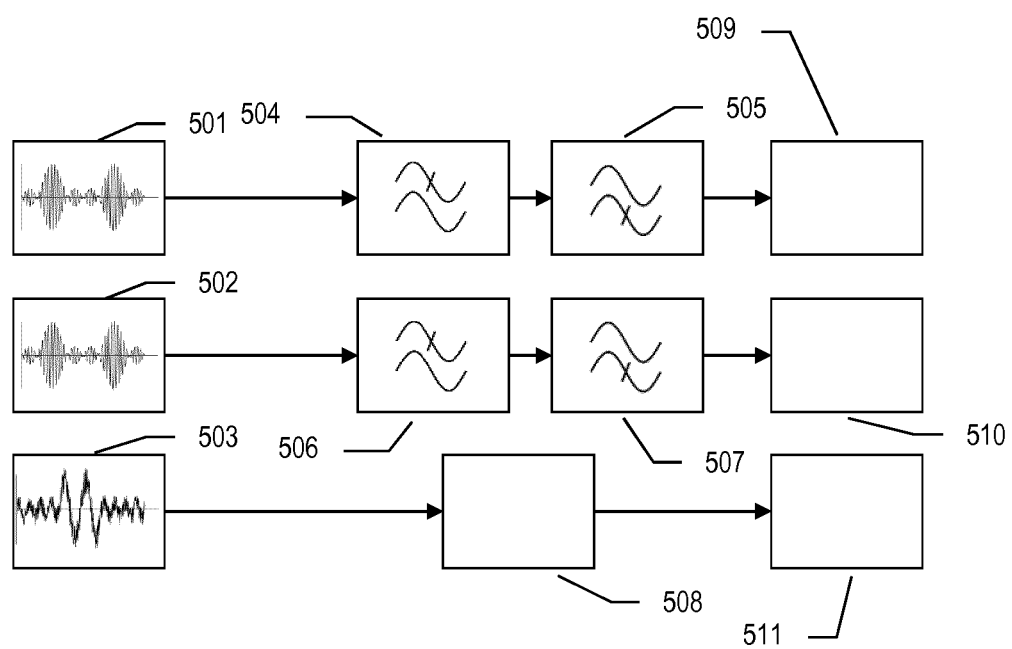
FIG. 5 shows the provisional signals processing operations.

FIG. 5 shows the provisional operations conducted on the input signals coming from the microphones (501, 502) and the motion sensors (503). The microphone signals (501, 502) are processed by means of a linear low-pass filter (504, 506) with a cut-off frequency of 3.5 kHz. Next, they are processed by means of a high-pass filter (505, 507) with a cut-off frequency of 150 Hz. The motion signals are smoothed out by means of a moving average filter (508) with a window length of 0.5 second. The result of pre-processing of the input signals are sound signals (509, 510) as well as acceleration and angular velocity signals (511).

Figure 6:
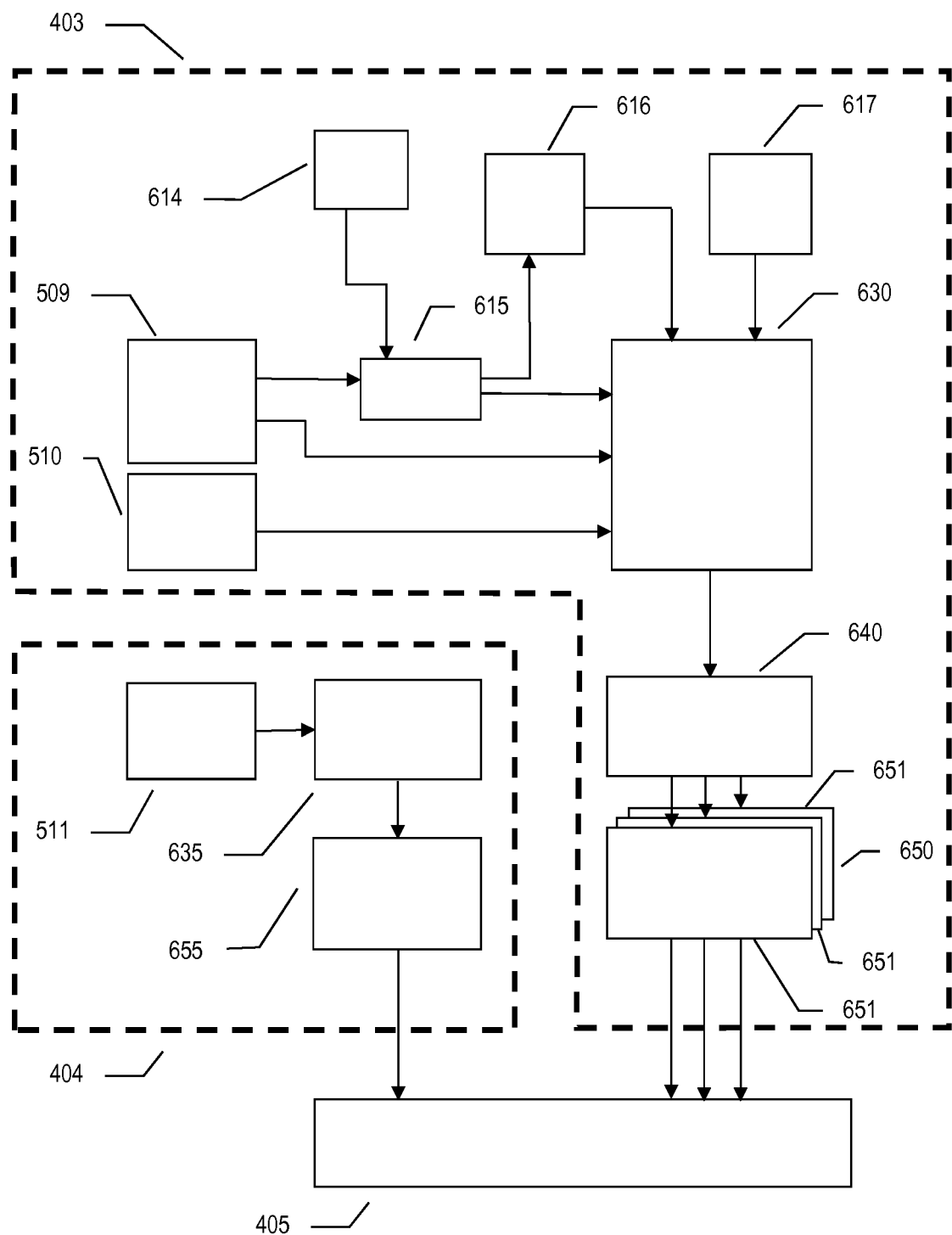
FIG. 6 shows the analysis circuits of sound signals and motion signals in the monitoring station according to the present disclosure.

FIG. 6 shows the analysis circuits (403, 404) of the sound signals (509, 510) and the motion signals (511). The algorithm of sound signals (509, 510) processing starts with cutting out segments of signals corresponding to respiratory episodes. On the basis of one sound signal (509) for a window defined by a clock signal (614), the segmentation module (615) designates the beginning and the end of the duration of a respiratory episode. For a given respiratory episode, the transformation module (630) creates an input vector (640), containing parameters calculated on the basis of sound signals (509, 510), for a detected respiratory episode as well as historical data (616) and statistical parameters (617). The input vector (640) is fed into the input of the classification module (650) which comprises three independent detection modules (651). The motion signals (511) processing algorithm starts with the parameterization of acceleration signals (coming from the accelerometer 635) and angular velocities (from the gyroscope 655). For short segments of signals coming from all axes, average values are determined which are used to determine the activity of the patient on the basis of the absolute value of a vector which is created once the effects of gravity have been removed.

The segmentation algorithm starts with the calculation of a signal spectrogram and, on the basis of the spectrogram, the determination of the sum of spectrum values for 20 frequency ranges divided into identical ranges up to a half of the sampling frequency value of the sound signal. However, it is possible to make a division into a different number of frequency ranges and the frequency ranges do not have to be the same. Signal portions, which exceed the threshold determined on the basis of the signal level for 10-second portions of signal duration, are pre-classified as episodes. Duplicates created as a result of overlapping of the 10-second portions are deleted. Episodes lasting longer than 3 seconds are divided into two separate episodes on the basis of the smallest value of the envelope of the signal in the range of 0.3-0.7 of the initial length of the episode. Episodes lasting less than 0.4 seconds are removed from the analysis. Over 10-second periods between the determined episodes are pre-designated as apnoea. Episodes lasting less than 0.5 seconds and whose time distance to at least one neighboring episode is more than 6 seconds are designated as respiratory-related events such as attempts to take a breath, swallow saliva, etc. The determined episodes serve as the basis for checking the quality of the recording. If there are less than 10 episodes in one minute of the recording, a message will be generated concerning a small number of the episodes detected. If there are more than 5 episodes with a duration greater than 0.5 seconds, this will generate a message concerning a large number of clicks in the signal. The value of the signal envelope that does not exceed an arbitrarily adopted threshold will cause a message to be generated concerning the low signal's amplitude level. An over-25-second break between two consecutive episodes will cause a message to be generated concerning an error in the recording of a specific signal segment.

The parametrizing, of all sound signals (509, 510) is carried out on the basis of the determined respiratory episodes. Portions of sound signals defined in such a manner make up sound episodes for each sound signal. The sound episodes coming from the first microphone (501) are used to calculate the following parameters: the average of the absolute value of the acoustic signal, the standard deviation of the absolute value of the acoustic signal, the three first maxima of the spectrum from the AR model determined using Burg's method, the average and standard deviation of the value of signal in the mel scale, the coefficients of the expected value to the minimum value and the maximum value to the minimum value—calculated for a sound episode extended by 5 seconds before and after the recording as well as for the parameters of the Linear Prediction Coding model. The sound episodes coming from the second microphone (502) are used to calculate the following parameters: the maximum amplitude of the signal, the average value of signal envelope and the three main formants.

Respiratory episode classification is based on the analysis of the calculated parameters by three three-layer neural networks which underwent individual learning. Each of those neural networks has one output neuron. The value of the signal on the output neuron corresponds to the classification of a sound episode by the network as snoring (for 1) or normal respiration (for 0). In order to obtain the final result of classification, the results of the individual networks take part in voting. In the case of consistent determination of an episode by all neural networks, the classification is final. In the case when there is no consistency as to the classification, the neural network result which is the closest to 0 or 1 is chosen for the final classification. If an episode classified as snoring lasts less than 0.5 seconds, it will be designated as a click. A median filter is used to remove current body position designations which last for very short periods of time.

The acoustic analysis is combined with the data specifying the motion and position of the body of the examined person during sleep. Signals from the three-axis acceleration sensor and the three-axis gyroscope are used to calculate the position of the body on the basis of a tree algorithm for the periods between the changes as well as to determine the motion on the basis of changes along one axis and between the axes. The position of the body is classified mainly as positions on the back, on the stomach, and on the side. This makes it possible to determine the positions in which there are snoring and apnoea episodes and when the noise may be classified as related to a change in position (these periods should be excluded from the analysis).

Motion signals are not subjected to segmentation. Parametrization of this signal is based on determining the geometric average of the signal for each axis for short signal segments, e.g. 50 ms, and, once the effects of gravity have been removed, determining the parameter corresponding to the 'activity' on the basis of the absolute value of a vector. Classification employing the acceleration signal and the angular velocity signal is based on the use of decision trees to determine the current position of the body for a specific signal segment. If the average absolute value of a vector in a time window is greater than the adopted threshold and if there is a change in the designations of the current position of the body between such a portion, then such a portion will be treated as a change in the position of the body and used in the interpretation of the acoustic signal.

Output signals from the respiratory events identification may be subjected to further statistical analysis. The analysis of results may include the following parameters: number of breaths—the total number of all episodes divided by 2 and the remainder after dividing by 2 as in the equation (1):

$$N_B = \left\lfloor \frac{n_e}{2} \right\rfloor + n_e \bmod 2 \qquad (1)$$

where: NB is the number of breaths and $n_e$ is the number of detected episodes;

number of snores—defined as the number of 'separate' snores (episodes classified as snoring which occur between two normal breaths) and 'aggregate' snores (episodes classified as snores which occur in the vicinity of other such episodes):

$$N_S = n_{SS} + \sum_{i=1}^{k} \left[ \left\lfloor \frac{n_{CS}(i)}{2} \right\rfloor + n_{CS}(i) \bmod 2 \right] \qquad (2)$$

where Ns is the number of snores, $n_{SS}$ is the number of separate snores, $n_{CS}(i)$ is the number of aggregate (collected) snores in the 'i' group and k is the number of groups;

snoring index—the sum of duration of all snoring episodes divided by the sum of duration of all episodes;

number of apnoeas—for adults, it is the number of breaks in respiration longer than 10 seconds (after the removal of non-classified periods);

apnoea index—the sum of duration of all apnoea episodes divided by the sum of duration of all breaks in respiration;

respiratory rate—the average distance between two respiratory episodes in a given unit of time.

Study results are based on presenting a graphical representation of the sound recorded by the first microphone along with the respiratory rate curve.

Moreover, the results analysis algorithm automatically determines the quality of sound by calculating parameters such as: the number of non-classified periods in the signal, numbers of non-classified periods that are too small, and high noise level. Periods of recording with bad sound quality are excluded from the analysis. However, if the signal from the first microphone is of good quality and the signal from the second microphone is of bad quality, the analysis will be conducted based on the good quality signal only.

Implementing the system into a mobile device, e.g. an application running on a mobile phone, makes it possible to have a short questionnaire filled out before the main measurement. The analysis of the main examination may be combined with a survey.

Figure 7:
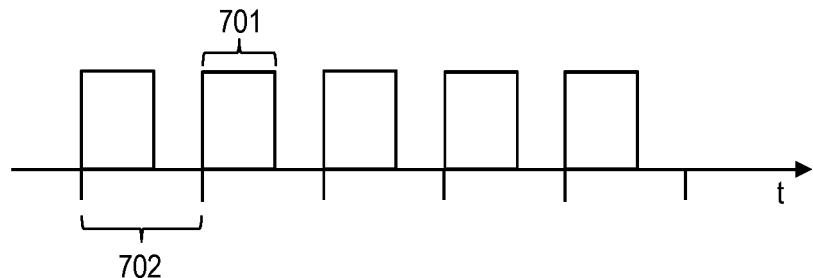
FIG. 7 shows the analysis process as a function of time.

FIG. 7 shows the analysis process (701) as a function of time relative to the period of measurement (702). Dividing the analysis process into small portions of the recorded signal makes it possible to obtain a result for the whole period of sleep immediately after waking up.

Figure 8:
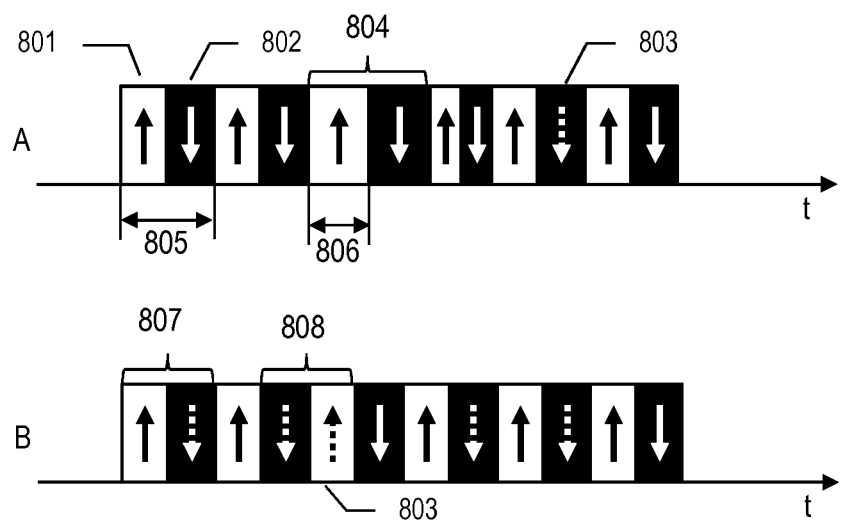
FIG. 8 shows model respiratory episodes cycles.

FIG. 8 shows two model cycles of episodes A and B. During the examination, the sensor detects respiratory episodes (801, 802, 803). The respiratory episodes may be classified as normal episodes of inhaling (801) or exhaling (802) or as a snoring episode (803). Two consecutively occurring, normal inhaling and exhaling episodes (801, 802) determine the number of full breaths (804). The time distance between two respiratory episodes (805), separated by a single respiratory event (806), determines the respiratory rate. Snoring episodes (803) may be defined as 'separate' snoring episodes (807) or as a group of 'aggregate' snoring episodes (808) which consists of consecutively occurring snoring episodes (803).

The invention claimed is:

1. A method for identifying respiratory events whereby,
    sound signals and a motion signal, which are generated during respiration, are recorded by a wireless sensor equipped with two microphone sensors and a motion sensor;
    signals from the sensors are converted into a digital data stream by a microcontroller;
    the digital data stream is sent to a monitoring station by a wireless transmission module;
    wherein, the digital data stream from the wireless sensor is received in the monitoring station and then digital data representing sound and motion signals are pre-filtered;
    in a segmentation module, the digital data representing a sound signal are divided into time windows and transformed to a frequency domain and then the sound signal is divided into segments corresponding to respiratory episodes on the basis of signal changes in the frequency domain in the time windows of the sound signal for specific sound signal frequencies;
    a first input vector is created combining sound signal parameters in a time domain and in the frequency domain, as well as statistical parameters specified on the basis of historical data, and a second input vector is created combining motion signal parameters in the time domain;
    the first input vector is fed into inputs of an assembly of at least three independent and different detection modules, which each have been designed to generate a signal classifying a respiratory event on the basis of the first input vector;
    the second input vector is fed into an input of a motion signals classification module which has been designed to generate a motion/position classification signal; and
    the parameters of two input sound signals in the time domain from the two microphone sensors, the motion signal parameters in the time domain from the motion sensor, at least three signals classifying the respiratory event from the at least three detection modules, and the motion/position classification signal are fed into an inference module which outputs a respiratory event identification signal.

2. The method of claim 1 wherein each of the at least three detection modules is a multi-layer neural network whose weights have been set in such a manner that a signal, which differentiates respiratory disorders from normal respiration, is generated at the output of the multi-layer neural network and contains a relative confidence factor of identification of respiratory disorders, and whereby in each detection module, the weights of neural networks have been selected independently from the weights of neural networks in other detection modules.

3. The method of claim 2 wherein a respiratory disorders signal is generated correspondingly to a reading of the detection module which generates an output signal with a highest confidence factor from the relative confidence factors.

4. The method of claim 1 wherein the first input vector is created in which the statistical parameters refer to the historical data of a population.

5. The method of claim 1 wherein the first input vector is created in which the statistical parameters refer to the historical data of an examined individual.

6. The method of claim 1 wherein the wireless sensor is equipped with a vibratory signalling device.

7. The method of claim 1 wherein the wireless sensor is equipped with a reflectance-based pulse oximeter.

8. A system for identifying respiratory events during examination constructed from
a wireless sensor comprising:
two microphone sensors and a motion sensor, which record sound signals and a motion signal generated during respiration,
a microcontroller, which converts signals from the sensors into a digital data stream, and
a first wireless transmission module;
a monitoring station comprising:
a second wireless transmission module;
a signals pre-processing module, which has been designed to pre-filter the data stream from the second wireless transmission module, divided into time windows, and transforms both the sound signals and the motion signal into a frequency domain for subsequent time windows;
segmentation modules, which have been designed to divide the sound signals and the motion signal into segments corresponding to respiratory episodes on the basis of sound signal changes in the frequency domain as well as into sound signal and motion signal time windows;
transformation modules, which have been designed to create a first input vector combining sound signal parameters in the time and frequency domains, as well as statistical parameters specified on the basis of historical data, and to create a second input vector combining motion signal parameters in the time domain;
a classification module, consisting of at least three independent and different detection modules which each have been designed to generate a signal classifying a respiratory event on the basis of the first input vector;
a motion signal classification module, which has been designed to generate a motion/position classification signal on the basis of the second input vector; and
an inference module, which has been designed to accept input of the parameters of two input sounds signals in the time domain from the two microphone sensors, the motion signal parameters in the time domain from the motion sensor, at least three signals classifying the respiratory event from the at least three detection modules, and the motion/position classification signal, and to output a respiratory event identification signal.

9. The system of claim 8 wherein each of the at least three detection modules is a multi-layer neural network whose weights have been set in such a manner that a signal, which differentiates respiratory disorders from normal respiration, is generated at the output of the neural network and contains a relative confidence factor of identification of respiratory disorders, and whereby in each detection module, the weights of neural networks have been selected independently from the weights of neural networks in other detection modules.

10. The system of claim 9 wherein each detection module has a different set of weights of neural networks.

11. The system of claim 9 wherein the inference module is adapted to generate a respiratory disorders signal based on the detection module with the highest confidence factor of the output.

12. The system of claim 9 wherein the motion sensor is an accelerometer/gyroscope or a combination of these two sensors.

13. The system of claim 9 wherein a sound signal is obtained from a microphone sensor or a signal coming from the motion sensor.

14. The system of claim 9 wherein the wireless sensor is equipped with a vibratory signalling device.

15. The system of claim 9 wherein the wireless sensor is equipped with a reflectance-based pulse oximeter.

16. The system of claim 9, wherein the statistical parameters of the first input vector refer to the historical data of an examined individual and/or population.

* * * * *